United States Patent [19]

Nojiri et al.

[11] Patent Number: 4,642,360
[45] Date of Patent: Feb. 10, 1987

[54] METHOD FOR PRODUCING ETHYLENE OXIDE

[75] Inventors: Naohiro Nojiri; Yukio Sakai, both of Ibaraki, Japan

[73] Assignee: Mitsubishi Petrochemical Co., Ltd., Tokyo, Japan

[21] Appl. No.: 782,178

[22] Filed: Oct. 1, 1985

Related U.S. Application Data

[63] Continuation of Ser. No. 592,370, Mar. 22, 1984, abandoned.

[30] Foreign Application Priority Data

Apr. 12, 1984 [JP] Japan .................................. 58-63909

[51] Int. Cl.$^4$ ............................................. C07D 301/10
[52] U.S. Cl. ..................... 549/534; 501/128; 501/133
[58] Field of Search ................. 549/534; 501/128, 133

[56] References Cited

U.S. PATENT DOCUMENTS

| | | | |
|---|---|---|---|
| 3,533,738 | 10/1970 | Rundell et al. | 501/128 |
| 3,826,813 | 7/1974 | Gardner et al. | 501/128 |
| 4,061,659 | 12/1977 | Nielsen et al. | 549/534 |
| 4,376,209 | 3/1983 | Watanabe et al. | 549/534 |

Primary Examiner—William R. Dixon, Jr.
Assistant Examiner—Steven Capella
Attorney, Agent, or Firm—Oblon, Fisher, Spivak, McClelland & Maier

[57] ABSTRACT

A packing material for a reactor for producing ethylene oxide by the catalytic oxidation of ethylene in the presence of molecular oxygen, wherein the packing material is used at the inlet side of a catalyst layer of the reactor, is silica-alumina containing 10 to 8 wt. % of silica, and is produced by sintering the silica-alumina at 1200° to 1500° C.

4 Claims, No Drawings

METHOD FOR PRODUCING ETHYLENE OXIDE

This application is a continuation of application Ser. No. 592,370, filed Mar. 22, 1984, now abandoned.

FIELD OF THE INVENTION

The present invention relates to a packing material which is filled at the inlet side of a fixed-bed catalytic reactor for producing ethylene oxide. The packing material of this invention does not poison a catalyst layer and can prevent increase of pressure loss in the reactor due to powdering of the packing material.

BACKGROUND OF THE INVENTION

A process of obtaining ethylene oxide by supplying a feedstock gas containing ethylene and molecular oxygen to a fixed bed comprising a silver catalyst filled in a multi-tube reactor and conducting the reaction at a temperature of 200° to 300° C. has been the only practical industrial process as a process for producing ethylene oxide by oxidation of ethylene with molecular oxygen. It is known that a refractory material is filled in the upstream part of the catalyst-filled bed as a preheating layer to elevate the temperature of the feedstock gas to the prescribed temperature.

The refractory material (packing material) must have the following two requirements: It should not break nor powder when packed or in use and it should not expose the elute sulfur, silicon, alkali metals (e.g., potassium), alkaline earth metals, and heavy metals (e.g., iron or copper) which cause poisoning the catalyst or side reactions other than the desired reaction. The former can be judged by the measurement of the compressive strength, and the latter can be evaluated by the measurement of the solubility in acid. A desirable packing material has higher compressive strength and lower solubility in acid.

Recently, the performance of the silver catalyst has been greatly improved and this means that the improved catalyst is more sensitive to the presence of other elements. Therefore, of the requirements for the packing material in the preheating layer, the latter requirement is particularly severe and high purity alumina which is substantially free of silicon is recently used.

However, a sintered product of high purity alumina is difficult to obtain a high strength and of the requirements for the packing material, the former requirement is not always satisfied. As a result, various problems are encountered that the overall pressure loss in the reactor increases, the local resistance increases and the catalyst does not uniformly contributes to reaction, leading to hot spots. The required strength can, of course, be obtained by sintering at high temperature (e.g., more than 1500° C.), but such is uneconomical. Thus high purity alumina is used without overcoming the above various problems. Further, even if a packing material having a satisfactory strength can be obtained, the problem still remains that elements such as sodium, aluminum, iron, etc. which might poison the silver catalyst tend to be eluted.

SUMMARY OF THE INVENTION

As a result of extensive investigations to develop a packing material which is free of the above-described disadvantages, this invention has be attained.

Accordingly, an object of this invention is to provide a packing material for a reactor for producing ethylene oxide by the catalytic oxidation of ethylene in the presence of molecular oxygen, wherein the packing material is used at the inlet side of a catalyst layer of the reactor, is silica-alumina containing 10 to 80 wt% of silica and is produced by sintering the silica-alumina at 1200° to 1500° C.

DETAILED DESCRIPTION OF THE INVENTION

The packing material of this invention is silica-alumina containing 10 to 80 wt%, preferably 30 to 75 wt%, of silica. The packing material is usually molded into spheres, tablets or cylinders, although varying depending on the size and form of the reactor tube. The size of the molding is, represented as spheres, several millimeters to several centimeters, preferably 3 to 15 mm, in diameter.

The packing material of this invention is produced by sintering the above-described moldings at 1200° to 1500° C. Sintering at a temperature lower than this range does not provide a sufficiently inert packing material and sintering at a temperature higher than this range is not economically desirable and causes silica to melt during sintering. In either cases, any satisfactory packing material cannot be obtained.

DESCRIPTION OF THE INVENTION

The packing material of this invention can increase its inertness as the content of silica increases. Therefore, the remainder is mainly alumina, but impurities such as sodium and iron are permissible so long as their content is about 2 wt% or less. These impurities can be sealed in the packing material in a quite inert state by sintering at 1200° to 1500° C. It is preferred that the packing material has a low porosity and does not have an acidity. This can be accomplished by properly selecting the compositions and sintering conditions.

The packing material of this invention can be also filled in the outlet side of the catalyst layer. The packing material to be filled in the outlet side is required to have sufficient strength to resist to powdering and to be inert to ethylene oxide formed. Thus, the packing material should not expose and elute a material which is chemically active to ethylene oxide. The packing material of this invention was found to meet these requirements. That is, it does not have acidity and does not elute iron etc.

In general, a reaction contains 0.1 to several % of water and carbon dioxide gas. Of high purity alumina packing materials, some materials have the inertness before use but lose the inertness by the action of those materials and/or heat. The packing material of this invention maintains the inertness even after use for a long period of time.

This invention will be now described in greater detail by reference to the following examples, but is not limited thereto.

EXAMPLES

Each of spherical packing materials having the compositions shown in Table 1 below was filled in the upstream side (top) and the downstream side (bottom) of a catalyst-filled bed of a multi-tube reactor for producing ethylene oxide. The overall height including the catalyst layer is about 12 m; the length of the upstream packing material layer is about 2 m and the length of the downstream packing material layer is about 50 cm.

In Table 1. Packing materials A and B are the invention, and packing materials C, D, and E are comparative examples.

The temperature of the catalyst layer was maintained at 230° to 250° C. and a reaction gas containing 28 vol% ethylene, 8.0 vol% oxygen and a small amount of an organohalide was passed at a space velocity (SV) of 4000 per hour. The ethylene oxide concentration at the outlet of reactor was a high yield of about 2%.

After operation for one year, the reactor tube filled with packing material A, B or E did not show any change but the height of the packing layer decreased a little in the case of packing material C and about 5 cm in the case of packing material D. The packing materials were taken out. Packing material D, particularly the material filled at the top, was found worn and deformed. This indicates that the packing material was powdered and lost during its use.

TABLE 1

| | Packing Material | | | | |
|---|---|---|---|---|---|
| | A | B | C | D | E |
| Particle diameter (mm) | 13 | 13 | 13 | 13 | 13 |
| Composition (wt %) | | | | | |
| $SiO_2$ | 73 | 31 | 0.05 | 0.2 | 0.02 |
| $Al_2O_3$ | 21 | 66 | 99.9 | 99.5 | 99.6 |
| $Fe_2O_3$ | 0.7 | 0.7 | 0.03 | 0.15 | 0.04 |
| $Na_2O$ | 1.2 | 0.6 | 0.02 | 0.01 | 0.30 |
| Sintering temperature (°C.) | 1300 | 1300 | 1500 | 1400 | 1600 |
| Apparent porosity (%) | 0.15 | 0.40 | 43 | 52 | 20 |
| Acidity (pka 4.8)* | None | None | None | Yes | None |
| Compressive strength (kg) | 290 | 520 | <100 | <70 | 370 |

*Shown by the color change of an indicator (pka = 4.8).

Each packing material prepared as above was subjected to acid dissolution test before and after its use. The results obtained are shown in Table 2. The values in Table 2 are the concentrations (in wt ppm) of the elements which dissolved in nitric acid. The concentrations thereof were measured by heating 10 g of sample in 50 ml of nitric acid (3 parts by voulume of conc. nitric acid and 1 part by volume of water) for 4 hours and diluting the resulting solution to 50 ml. A considerable amount of dissolution of Na and Al took place in the cases of packing materials C and D and even in the case of packing material E which has high compressive strength. Dissolution of Al and P was observed in the case of packing material D. Very slight dissolution was observed in packing materials A and B.

The reaction results support the above-described facts, and packing materials A and B were completely inactive to the reaction. Packing material D yielded aldehyde and the yield increased with the passage of time.

A packing material having the same compositions as in the packing material A was sintered at 1120° C. (outside the sintering temperature range of the invention) to obtain a packing material F having a particle diameter of 13 mm. The packing material F had an apparent porosity of 9.2% and a compressive strength of 230 kg. Using the packing material F, the acid dissolution test was conducted in the same manner as described above.

The results obtained are shown in Table 3 below. For the sake of comparison the results of the packing material A are also shown.

The results shown in Table 2 and 3 clearly demonstrate that the packing material of this invention is a material having a high strength and no acid dissolution property.

TABLE 2

| Element | | Packing Material | | | | |
|---|---|---|---|---|---|---|
| | | A | B | C | D | E |
| Al | Before use | <2 | 15 | 110 | 1200 | 200 |
| | After use | <2 | 15 | 110 | 1600 | 200 |
| Si | Before use | nd | nd | tr | tr | tr |
| | After use | nd | nd | tr | tr | tr |
| Na | Before use | 0.2 | 0.4 | 30 | 60 | 170 |
| | After use | 0.2 | 0.4 | 30 | 60 | 170 |
| Fe | Before use | 0.03 | 0.06 | 0.3 | 9 | 0.1 |
| | After use | 0.03 | 0.06 | 0.3 | 9 | 0.1 |
| K | Before use | 0.1 | 0.3 | 3 | 20 | 0.3 |
| | After use | 0.1 | 0.3 | 3 | 20 | 0.3 |
| P | Before use | <0.5 | <0.5 | <0.5 | 40 | <0.5 |
| | After use | <0.5 | <0.5 | <0.5 | 60 | <0.5 |

Note:
nd: not detected
tr: trace

TABLE 3

| Packing Material | Element | | | | |
|---|---|---|---|---|---|
| | Al | Si | Na | Fe | K |
| F | 48 | <5 | 67 | 5 | 4.3 |
| A | <2 | nd | 0.2 | 0.03 | 0.1 |

Note:
nd: not detected

What is claimed is:
1. A method for producing ethylene oxide, which comprises:
    passing a feedstock gas of ethylene and molecular oxygen through a reactor containing a packing material of silica-alumina containing 10–80 weight percent of silica which has been sintered at 1200°–1500° C. in order to preheat said feed stock gas, and then through a catalyst bed which catalyzes the reaction of ethylene with molecular oxygen to produce said ethylene oxide.
2. The method of claim 1, wherein the silica-alumina contains 30 to 80% by weight of silica.
3. The method of claim 1, wherein the temperature of said reaction ranges from 230° to 250° C.
4. The method of claim 1, wherein said silica-alumina packing material contains impurities in amounts of no more than 2 weight percent.

* * * * *